(12) United States Patent
Lu et al.

(10) Patent No.: US 9,918,971 B2
(45) Date of Patent: Mar. 20, 2018

(54) AEROSOL FORMULATIONS OF GRANISETRON AND USES THEREOF

(71) Applicant: LUXENA PHARMACEUTICALS, INC., Sunnyvale, CA (US)

(72) Inventors: George Lu, Palo Alto, CA (US); Xiaodong Li, Sunnyvale, CA (US); Biao Lu, Palo Alto, CA (US)

(73) Assignee: LUXENA PHARMACEUTICALS, INC., Sunnyvale, CA (US)

( * ) Notice: Subject to any disclaimer, the term of this patent is extended or adjusted under 35 U.S.C. 154(b) by 0 days.

(21) Appl. No.: 15/156,796

(22) Filed: May 17, 2016

(65) Prior Publication Data

US 2016/0331732 A1 Nov. 17, 2016

Related U.S. Application Data

(63) Continuation of application No. 14/323,089, filed on Jul. 3, 2014, now abandoned.

(60) Provisional application No. 61/842,825, filed on Jul. 3, 2013, provisional application No. 61/909,982, filed on Nov. 27, 2013.

(51) Int. Cl.
*A61K 9/14* (2006.01)
*A61K 31/439* (2006.01)
*A61K 31/46* (2006.01)
*A61K 9/00* (2006.01)
*A61K 9/16* (2006.01)
*A61K 47/26* (2006.01)

(52) U.S. Cl.
CPC ............ *A61K 31/439* (2013.01); *A61K 9/008* (2013.01); *A61K 9/0075* (2013.01); *A61K 9/1623* (2013.01); *A61K 31/46* (2013.01); *A61K 47/26* (2013.01)

(58) Field of Classification Search
USPC .......................................................... 424/489
See application file for complete search history.

(56) References Cited

U.S. PATENT DOCUMENTS

2007/0178166 A1* 8/2007 Bernstein ............. A61K 9/0043
424/499
2015/0010633 A1 1/2015 Xiaodong et al.

OTHER PUBLICATIONS

Aapro., "Granisetron: an update on its clinical use in the management of nausea and vomiting.", 2004, 9(6), 673-86.
Chow; et al., "Particle engineering for pulmonary drug delivery.", Mar. 2007, 24(3), 411-37.
Cooke; et al., "Oral ondansetron for preventing nausea and vomiting.", Mar. 15, 1994, 51(6), 762-71.
Hornby., "Central neurocircuitry associated with emesis.", Dec. 3, 2001, 111 Suppl 8A, 106S-112S.
Office action dated Mar. 19, 2015 for U.S. Appl. No. 14/323,115.
Ye; et al., "Ondansetron: a selective 5-HT(3) receptor antagonist and its applications in CNS-related disorders.", 2001 Summer, 7(2), 199-213.
U.S. Appl. No. 14/323,115, filed Jul. 3, 2014, Li, et al.

* cited by examiner

*Primary Examiner* — Devang Thakor

(57) ABSTRACT

Aerosol formulations of granisetron useful for pulmonary delivery are provided. The formulations are useful in the reduction, elimination or prevention of nausea and vomiting associated with chemotherapy, radiation therapy, and surgery. Also provided are novel methods to treat chemotherapy-induced nausea and vomiting (CINV), radiation-induced nausea and vomiting (RINV), and post-operative nausea and vomiting (PONV) using the inhalation formulations.

13 Claims, 9 Drawing Sheets

|   | File | Dx(10) | Dx(50) | Dx(90) |
|---|---|---|---|---|
| [V] | granisetron_5th mill | 1.59 | 3.79 | 8.13 |
| [V] | granisetron_3rd mill | 1.44 | 3.99 | 9.90 |
| [V] | granisetron_1st mill | 2.22 | 7.01 | 20.59 |
| [V] | granisetron_unmilled | 3.77 | 50.21 | 445.02 |

[V]=Volume [N]=Number

AEROSOL FORMULATIONS OF GRANISETRON AND USES THEREOF

CROSS-REFERENCE TO RELATED APPLICATIONS

The present application is a Continuation of co-pending U.S. Non-Provisional application Ser. No. 14/323,089 filed Jul. 3, 2014, which in turn, claims the benefit under 35 U.S.C. § 119 of U.S. Provisional Application Ser. No. 61/842,825, filed on Jul. 3, 2013, and U.S. Provisional Application Ser. No. 61/909,982, filed on Nov. 27, 2013, the contents of which applications are hereby incorporated herein by reference in their entireties.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF THE MATERIAL ON THE COMPACT DISC

Not Applicable.

BACKGROUND OF THE INVENTION

Field of the Invention

Provided herein are novel aerosol inhalation formulations of granisetron for pulmonary delivery; and uses thereof in the reduction, elimination or prevention of nausea and vomiting associated with chemotherapy, radiation therapy and surgery. Also provided are methods to treat chemotherapy-induced nausea and vomiting (CINV), radiation-induced nausea and vomiting (RINV), and post-operative nausea and vomiting (PONY) using the inhalation formulations.

Description of the Related Art Including Information Disclosed Under 37 CFR 1.97 and 1.98

Cancer is one of the major causes of death in the modern world. Major therapies to treat cancers include chemotherapy, radiation therapy and surgery. Nausea and vomiting are among the most common side-effects of these treatments. Patients receiving highly emetogenic agents may postpone, or even refuse, potentially curative treatments. Increasing of blood level of serotonin and activation of the 5-$HT_3$ receptors in the chemoreceptor trigger zone in the brain are believed to be related to the emetic responses to cancer treatments [Hornby, 2001].

Granisetron is a 5-$HT_3$ receptor antagonist used mainly as an antiemetic often following chemotherapy, radiation therapy and surgery. Granisetron is believed to block 5-$HT_3$ receptors in the chemoreceptor trigger zone. It is believed to reduce the activity of the vagus nerve, hence the compound deactivates the vomiting center in the medulla oblongata [Aapro, 2004]. FIG. 1 shows the skeletal formula of granisetron.

Currently, granisetron is administered either through injection (slow IV or IM) or as oral tablets. Injection of granisetron, although effective in reducing or preventing nausea and vomiting, is inconvenient, invasive and causes pain to the patients. Existing forms of oral granisetron tablets can be difficult to swallow and may be undesirable to some patients requiring anti-emetic therapy, especially those patients who have severe nausea or vomiting.

Thus, there remains a need for new formulations and for novel methods to administer granisetron. The formulations, and methods described herein are directed toward this end.

BRIEF SUMMARY OF THE INVENTION

In one aspect, the present invention provides novel aerosol formulations comprising granisetron useful for pulmonary delivery to a subject. In one embodiment, the aerosol formulations are administered by inhalation. In another embodiment, the aerosol formulations are delivered into the circulation via the pulmonary tract. In one embodiment, the subject is a patient such as a cancer patient.

In certain aspects, the present invention provides pharmaceutical aerosol inhalation formulations comprising granisetron.

In certain aspects, the aerosol formulations of the present invention are useful for the reduction, elimination or prevention of various medical conditions including chemotherapy-induced nausea and vomiting (CINV), radiation-induced nausea and vomiting (RINV), and post-operative nausea and vomiting (PONV).

In another aspect, the present invention provides methods of treating a condition of nausea or vomiting, wherein the method comprises pulmonary administration of a pharmaceutically acceptable amount of the aerosol formulations of the present invention, and wherein the aerosol formulations are administered into the pulmonary tract by inhalation.

In yet another aspect, the present invention provides methods for pulmonary delivery of granisetron to a subject that comprise having the subject inhale a pharmaceutically acceptable amount of the aerosol formulation of the present invention through the subject's mouth into the circulation via the pulmonary tract. In one embodiment, the subject is a cancer patient.

In yet another aspect, the present invention provides a method for pulmonary delivery of granisetron to a subject, where the method comprises having the subject inhale a pharmaceutically acceptable amount of the aerosol formulation of the present invention through the subject's nose into the circulation via the pulmonary tract. In one embodiment, the subject is a cancer patient.

In yet another aspect, with respect to the aerosol formulations or methods of the present invention, the pulmonary administration of the aerosol formulations minimizes the first pass metabolism before the drug reaches the target receptors since there is rapid transport from the alveolar epithelium into the circulation. In addition, the pulmonary administration of the aerosol formulations of the present invention by inhalation avoids gastrointestinal intolerance which is typical for nausea and vomiting sufferers.

Other objects and advantages will become apparent to those skilled in the art from a consideration of the ensuing detailed description.

DETAILED DESCRIPTION OF THE INVENTION

Figure 1:
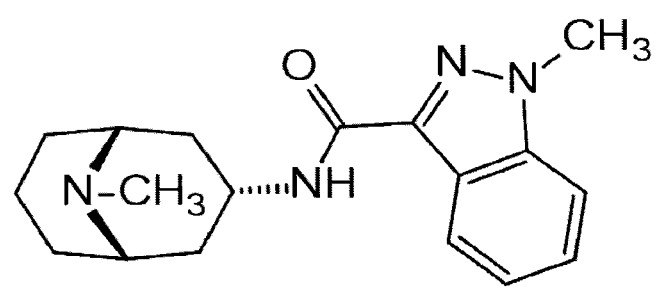
FIG. 1: Skeletal Formula of Granisetron

The present invention provides novel aerosol formulations comprising granisetron useful for pulmonary delivery to a subject. In one embodiment, the aerosol formulations are administered by inhalation. In another embodiment, the aerosol formulations are delivered into the circulation via the pulmonary tract. The subject for whom the aerosol formulations are administered may be a mammal, such as a human. In one embodiment, the subject is a patient; in particular, the subject is a cancer patient.

The present invention also provides pharmaceutical aerosol inhalation formulations comprising powdered granisetron. In one embodiment, with respect to the aerosol inhalation formulation, the mass median aerodynamic diameter (MMAD) of powdered granisetron is between 0.05 and 20 microns, preferably the powdered granisetron has an MMAD between 0.5 and 5 microns. In another embodiment, the aerosol formulations are useful for pulmonary delivery of granisetron to a subject. In one embodiment, the subject is a cancer patient.

In addition, the present invention provides inhalable pharmaceutical aerosol formulations comprising powdered granisetron, wherein the MMAD of powdered granisetron is between 0.05 and 20 microns; and wherein the formulations are useful for pulmonary delivery to a subject, where the subject is a cancer patient. In one embodiment, the aerosol formulations are delivered into the circulation via pulmonary tract of the subject and the subject is a cancer patient.

In certain aspects, the aerosol formulations of the present invention are useful for the reduction, elimination, or prevention of nausea and vomiting associated with various medical conditions including chemotherapy-induced nausea and vomiting (CINV), radiation-induced nausea and vomiting (RINV), and post-operative nausea and vomiting (PONV).

In certain aspects, the aerosol formulations of the present invention are administered by subjects via an inhaler allowing granisetron to enter the circulation rapidly.

In certain aspects, the aerosol formulations of the present invention provide a novel route of administration of granisetron to subjects who have severe nausea or vomiting and not willing to or not able to swallow or to be injected.

In certain aspect, the aerosol formulations of the present invention contains granisetron that is in a solute form. In certain aspect, the aerosol formulations of the present invention contains granisetron that is in a powdered form.

In certain aspect, the aerosol formulations of the present invention contains granisetron that is in a powdered form, and the powdered granisetron is in a dry powder form.

In certain aspect, the aerosol formulations of the present invention contains granisetron that is in a powdered form, and the powdered granisetron is in a suspension. In certain aspect, the powdered granisetron suspension is in a liquid selected from a group consisting of propellants, hybrid propellants, propellants with stabilizers, propellants with surfactants, propellants with diluents, propellants with cosolvents, water, buffer, and combinations thereof.

In certain aspect, the aerosol formulations of the present invention contains granisetron that is a solute in a solution, and the solvent is selected from a group consisting of propellants, hybrid propellants, cosolvents, cosolvent mixture, organic solvents, water, buffers, and combinations thereof.

When the granisetron in the aerosol formulations is in a powdered form, the powdered granisetron is produced by one or more particle engineering processes [Chow et al., 2007]. For example, the powdered granisetron may be produced by a mechanical micronization operation selected from the group consisting of crushing, cutting, bashing, milling, and grinding. In another embodiment, the powdered granisetron is produced by a precipitation process, such as spray drying, solution precipitation, lyophilization, or combinations of the foregoing. Yet in another embodiment, the powered granisetron is produced by one of more precipitation processes followed by one or more mechanical micronization processes.

In one embodiment, the powdered granisetron of the aerosol formulations is produced by a spray drying process. The spray drying process may be followed by a cyclone separation/filtering process.

In another embodiment, the powdered granisetron of the aerosol formulations is produced by a direct controlled crystallization process. The direct controlled crystallization process may utilize an antisolvent precipitation technique. Moreover, the size range of the crystallines may be controlled by one or more growth-retarding stabilizing additives.

In yet another embodiment, the powdered granisetron of the aerosol formulations is produced by a supercritical fluid process. The supercritical fluid process is selected from the group consisting of rapid expansion of supercritical solution (RESS), solution enhanced diffusion (SEDS), gas-anti solvent (GAS), supercritical antisolvent (SAS), precipitation from gas-saturated solution (PGAS), precipitation with compressed antisolvent (PCA) and aerosol solvent extraction system (ASES).

In a particular embodiment, with respect to the aerosol formulations, the powdered granisetron is produced by supercritical fluid process, and the process is rapid expansion of supercritical solution (RESS) process. In another particular embodiment, the process is solution enhanced diffusion (SEDS) process. In yet another particular embodiment, the process is gas-anti-solvent (GAS) process. In yet another particular embodiment, the process is supercritical-anti-solvent (SAS) process. In yet another particular embodiment, the process is precipitation from gas-anti-solvent (PGAS) process. In yet another particular embodiment, the process is precipitation with compressed anti-solvent (PCA) process. In yet another particular embodiment, the process is aerosol solvent extraction system (ASES) process. In yet another particular embodiment, the process is any combinations of the foregoing.

In a more particular embodiment, with respect to the aerosol formulations, the powdered granisetron is produced by a supercritical fluid process, and the supercritical fluid process is rapid expansion of supercritical solution process.

In one embodiment, with respect to the aerosol formulations, the mean geometric diameter of powdered granisetron is at least 0.01 microns, at least 0.05 microns, at least 0.1 microns, at least 0.25 microns, at least 0.5 microns, at least 0.75 microns, at least 0.9 microns, at least 1 microns, at least 1.25 microns, at least 1.5 microns, at least 1.75 microns, or even at least 2.0 microns. The mean geometric diameter of powdered granisetron is at most 20 microns, at most 15 microns, at most 12 microns, at most 10 microns, at most 9 microns, at most 8 microns, at most 7.5 microns, at most 7 microns, at most 6.5 microns, at most 6.0 microns, at most 5.75 microns, at most 5.5 microns, at most 5.25 microns, at most 5.0 microns, at most 4.75 microns, at most 4.5 microns, at most 4.25 microns, at most 4.0 microns, at most 3.75 microns, at most 3.5 microns, at most 3.25 microns, and even at most 3.0 microns. The mean geometric diameter of powdered granisetron generally ranges from between 0.05 and 30 microns, preferably between 0.1 and 20 microns, between 0.2 and 15 microns, between 0.3 and 10 microns, and more preferably between 0.5 and 5 microns. Advantageously, the mean geometric diameter of powdered granisetron is between 1 and 3 microns.

In a particular embodiment, with respect to the aerosol formulations, the mean geometric diameter of powdered granisetron is between 0.05 and 20 microns, preferably between 0.5 and 4 microns, more preferably between 1 and 3 microns.

In one embodiment, with respect to the aerosol formulations, the powdered granisetron has an MMAD of at least 0.01 microns, at least 0.05 microns, at least 0.1 microns, at least 0.25 microns, at least 0.5 microns, at least 0.75 microns, at least 0.9 microns, at least 1 microns, at least 1.25 microns, at least 1.5 microns, at least 1.75 microns, or even at least 2.0 microns. The MMAD of powdered granisetron is at most 30 microns, at most 20 microns, at most 15 microns, at most 10 microns, at most 9 microns, at most 8 microns, at most 7.5 microns, at most 7 microns, at most 6.5 microns, at most 6.0 microns, at most 5.75 microns, at most 5.5 microns, at most 5.25 microns, at most 5.0 microns, at most 4.75 microns, at most 4.5 microns, at most 4.25 microns, at most 4.0 microns, at most 3.75 microns, at most 3.5 microns, at most 3.25 microns, and even at most 3.0 microns. Generally, the MMAD of the powdered granisetron is between 0.05 and 30 microns, preferably between 0.1 and 20 microns, between 0.2 and 15 microns, more preferably between 0.3 and 10 microns, between 0.5 and 5 microns, and especially between 1 and 3 microns.

In a particular embodiment, with respect to the aerosol formulations, the powdered granisetron has an MMAD between 0.05 and 20 microns, preferably between 0.5 and 4 microns, and more preferably between 1 and 3 microns.

In one embodiment, with respect to the aerosol formulations, the mean geometric diameter and the MMAD of powdered granisetron are similar. Alternatively, in another embodiment, the mean geometric diameter and the MMAD of powdered granisetron are different. In one embodiment, where the mean geometric diameter and the MMAD of powdered granisetron are different, the difference is due to the morphology of the granisetron particles.

The powdered granisetron may be a solvate, hydrate, organic salt, inorganic salt, ester, or free base. The powdered granisetron may also be amorphous, crystalline, or polymorphous. Preferably, the granisetron is a chloride, bromide, iodide, mesylate, methanesulphonate, para-toluenesulphonate, or methyl sulphate salt. More preferably, the granisetron is in the form of a hydrochloride, anhydrous, monohydrate or dihydrate.

In one embodiment, the granisetron particles of the aerosol formulations are amorphous.

In one embodiment, the granisetron particles of the aerosol formulations are crystallines. In another embodiment, the shape of the granisetron particles is one of the group consisting of spherical, ellipsoidal, cubical, diamond, rectangular, orthorhombic, triangular, hexagonal, needlelike, and porous. Preferably, the granisetron particles of the aerosol formulations are spherical.

In one embodiment, the granisetron particles of the aerosol formulations are polymorphous. In another embodiment, the shapes of the granisetron particles are two of more from the group consisting of spherical, ellipsoidal, cubical, diamond, rectangular, orthorhombic, triangular, hexagonal, needlelike, and porous.

In one embodiment, with respect to the aerosol formulations, the proportion of granisetron particles with aerodynamic diameters less than 5 µm is at least 5%, at least 10%, at least 15%, at least 20%, at least 25%, at least 30%, at least 35%, at least 40%, at least 45%, at least 50%, at least 55%, at least 60%, at least 70%, and preferably at least 70%. In another embodiment, the proportion of granisetron particles with aerodynamic diameters less than 5 µm is at most 100%, at most 99%, at most 95%, at most 90%, at most 85%, at most 80%, at most 75%, at most 70%, at most 65%, at most 60%, at most 55%, at most 50%, at most 45%, at most 40%, at most 35%, at most 30%, at most 25%, at most 20%, at most 17.5%, at most 15%, and even at most 12.5%.

In one embodiment, with respect to the aerosol formulations, the proportion of granisetron particles with aerodynamic diameters less than 5 µm is 10% to 100%, preferably from 70% to 100%. In another embodiment, the proportion of granisetron particles with aerodynamic diameters less than 5 µm is from 20 to 80%, preferably from 30% to 70%. In a further embodiment, the proportion of granisetron particles with aerodynamic diameters less than 5 µm is 10% to 30%.

In one embodiment, with respect to the aerosol formulations, the fine particle fraction (FPF) of granisetron is 10% to 100%. In certain embodiments, the minimum FPF is 50%, for instance, at least 55%, at least 60%, at least 65%, at least 70%, at least 75%, at least 80%, at least 85%, and even at least 90%. In one embodiment, the FPF of granisetron is from 70% to 100%. The FPF of granisetron may also range from 30% to 70%. In another embodiment, the maximum FPF of granisetron is 50% or less, for instance, the maximum FPF of granisetron is at most 40%, at most 35%, at most 30%, at most 25%, at most 20%, at most 17.5%, at most 15%, at most 12.5%, and even at most 10%. In one embodiment, the FPF of the granisetron is 10% to 30%.

In the aerosol formulations according to the invention, the granisetron has respirable fraction of 10% or more, preferably 15% or more, 20% or more, 25% or more, 35% or more, 40% or more, 45% or more, 50% or more, more preferably 75% or more, and even 90% or more.

In one embodiment, the aerosol formulations do not comprise an excipient.

In another embodiment, the aerosol formulations further comprise a pharmaceutically acceptable excipient. The excipient is any excipient acceptable for pulmonary delivery. More particularly, the excipient is any inhalable excipient.

In aerosol formulations containing an excipient, the excipient is selected from the group consisting of carbohydrates, amino acids, polypeptides, lipids, buffers, salts, polyalcohols, and mixtures thereof. In yet another embodiment, the excipient is selected from the group consisting of galactose, mannose, sorbose, lactose, glucose, trehalose, raffinose, maltodextrins, dextrans, mannitol, xylitol, and mixtures thereof. In yet another embodiment, the excipient is selected from the group consisting of alanine, glycine, tryptophan, tyrosine, leucine, phenylalanine, and mixtures thereof. In yet another embodiment, the excipient is selected from the group consisting of oleates, stearates, myristates, alkylethers, alkyl arylethers, sorbates, polyvinylpyrrolidone (PVP) and mixtures thereof. In yet another embodiment, the excipient is selected from the group consisting of 1,1,1,2-tetrafluoroethane (P134a), 1,1,1,2,3,3,3-heptafluoro-n propane (P227), 2H, 3H-perfluoropentane (HPFP) and mixtures thereof. In yet another embodiment, the excipient is any combinations of the foregoing.

In certain embodiments, the aerosol formulations are pressurized metered dose formulations. In certain embodiments, the aerosol formulations are dry powder formulations. In certain embodiments, the aerosol formulations are nebulizer formulations.

Dry Power Formulations

In a particular embodiment, the formulation is a dry powder formulation containing an excipient, where the excipient is lactose, glucose, or a mixture of lactose and glucose.

In the dry powder formulations containing a pharmaceutically acceptable excipient, the excipient consists of powders with an average particles size of <5 to 200 microns, from 1 to 150 microns, or from 5 to 100 microns. The excipient may consists of powders of the same substance with an average particle size of <5 to 200 microns, from 1 to 150 microns, or from 5 to 100 microns. There may also be a mixture of powders in which the average particle size is from <5 to 200 microns, from 1 to 150 microns, or from 5 to 100 microns.

In particular, where the dry powder formulations further comprise a pharmaceutically acceptable excipient and the excipient consists of powders with an average particle size of <5 to 200 microns, the excipient may be a mixture of the same substance with different particle size distributions. For example, in one embodiment the pharmaceutically acceptable excipient having an average particle size of <5 to 200 microns with different particle size distributions is a mixture of coarser powders and finer powders of the same substance, where the finer powders have an average particle size from <5 to 50 microns and the coarser powders have an average particle size of 50 to 200 microns. The finer powders may have an average particle size from <5 to 45 microns, from 10 to 40 microns, from 15 to 35 microns, or from 20 to 30 microns, while the coarser powders may have an average particle size from 60 to 90 microns, from 65 to 85 microns, or from 70 to 80 microns. Alternatively, the finer powders may have an average particle size from 1 to 10 microns, from 1 to 7.5 microns, from 1 to 5 microns, or from 2 to 5 microns, while the coarser powders may have an average particle size from 20 to 60 microns, from 20 to 25 microns, from 30 to 60 microns, from 40 to 60 microns, or from 50 to 60 microns. In some embodiments, the coarser powders have an average particle size from 50 to 90 microns, from 65 to 85 microns, or from 70 to 80 microns. The proportion of finer excipient powders may be 0.1% to 99% of the total amount of excipient powders.

In another embodiment, with respect to the dry powder formulations, the pharmaceutically acceptable excipient having an average particle size of <5 to 200 microns with different particle size distributions is a mixture of finer powders, coarser powders, and much coarser powders of the same substance, where the finer powders have an average particle size of <5 to 20 microns, the coarser powders have an average particles size of 20 to 60 microns, and the much coarser powders have an average particles size of 60 to 200 microns. Preferably, the finer powders have an average particle size of <5 to 10 microns, the coarser powders have an average particles size of 25 to 45 microns, and the much coarser powders have an average particles size of 75 to 90 microns. The proportion of finer excipient powders may be 0.1% to 99% of the total amount of excipient powders.

In addition, in the dry powder formulations, the pharmaceutically acceptable excipient may be a mixture of different substances with similar particle size distributions in which the average particle size is from <5 to 200 microns or from 5 to 100 microns.

Advantageously, the pharmaceutically acceptable excipient in the dry powder formulations is a mixture of different substances with different particle size distributions in which the average particle sizes are from <5 to 200 microns. Namely, the pharmaceutically acceptable excipient of the dry powder formulations is a mixture of finer powders having an average particle size of <5 to 50 microns and coarser powders with an average particles size of 50 to 200 microns; the finer powders and the coarser powders being different substances. The proportion of finer excipient powders may be 0.1% to 99% of the total amount of excipient powders.

In another embodiment, the pharmaceutically acceptable excipient of the dry powder formulations is a mixture of finer powders having an average particle size of <5 to 20 microns, coarser powders having an average particles size of 20 to 60 microns, and much coarser powders having an average particles size of 60 to 200 microns; the finer powders, the coarser powders, and the much coarser powders being different substances. Preferably, the finer powders have an average particle size of <5 to 15 microns, the coarser powders have an average particles size of 30 to 50 microns, and the much coarser powders have an average particles size of 70 to 90 microns. The proportion of finer excipient powders may be 0.1% to 99% of the total amount of excipient powders.

In embodiments where the pharmaceutically acceptable excipient of the dry powder formulations is a mixture of finer powders and coarser powders; the powdered granisetron may be blended with the finer excipient powders first, and then the mixture of the powdered granisetron and the finer powders are blended with the coarser excipient powders. Alternatively, the powdered granisetron may be blended with the finer excipient powders and the coarser excipient powders separately, and then each of the blended excipient mixtures (i.e., finer excipient powders with powdered granisetron and coarser excipient powders with powdered granisetron) are blended with each other.

In embodiments were the pharmaceutically acceptable excipient of the dry powder formulations is a mixture of finer powders, coarser powders, and much coarser; the powdered granisetron may be sequentially blended with the finer excipient powders, the coarser excipient powders, and the much coarser excipient powders. Alternatively, the powdered granisetron is blended with the finer excipient powders, the coarser excipient powders, and the much coarser excipient powders separately, and then the mixtures (i.e., finer excipient powders with powdered granisetron, coarser excipient powders with powdered granisetron, and much coarser excipient powders with granisetron) are blended with each other.

The content of the powdered granisetron in the dry powder formulations ranges from 0.05% to about 100% of the total composition of formulation, preferably from about 0.05% to about 50%, from about 0.05% to about 45%, from about 0.05% to about 40%, from about 0.05% to about 35%, from about 0.05% to about 30%, from about 0.05% to about 25%, from about 0.05% to about 20%, from about 0.05% to about 15%, or from about 0.05% to about 10% of the total composition of formulation.

The content of the powdered granisetron in the dry powder formulations may also range from about 0.1% to about 100%, from about 0.1% to about 50%, from about 0.1% to about 45%, from about 0.1% to about 40%, from about 0.1% to about 35%, from about 0.1% to about 30%, from about 0.1% to about 25% of the total composition of formulation, from about 0.1% to about 20%, from about 0.1% to about 15%, or from about 0.1% to about 10% of the total composition of formulation, preferably from about 1% to about 10% of the total composition of formulation, and more preferably from about 5% to about 10% of the total composition of formulation. In a particular embodiment, with respect to the formulations, the powdered granisetron is about 10% of the total composition of formulation.

Generally, the dry powder formulations contain 0.1-10 mg of the powdered granisetron, preferably from 0.5-5 mg, from 1-3 mg.

In a particular embodiment, the dry powder formulations comprise granisetron and lactose. The dry powder formulations containing lactose comprise granisetron, finer lactose, and coarser lactose, or granisetron, finer lactose, and much coarser lactose granisetron, or finer lactose, coarser lactose, and much coarser lactose. For example, the dry powder formulations may comprise about 0.5 to about 5 mg of granisetron, about 0.001 to about 2 g of finer lactose, and about 0.001 to about 2 g of coarser lactose. For example, in dry powder formulations containing granisetron and lactose or glucose, the amount of the granisetron is from 0.5-5 mg, and the amount of lactose or glucose is about 0.001 g to about 2.5 g. Preferably, the amount of granisetron is about 0.5 to about 5 mg and the amount of lactose or glucose is about 1 to about 200 mg.

In yet another particular embodiment, the dry powder formulations comprise granisetron and glucose. The dry powder formulations containing glucose comprise granisetron, finer glucose, and coarser glucose, or granisetron, finer glucose, coarser glucose, and much coarser glucose. In yet another particular embodiment, the dry powder formulations comprise about 0.5 to about 5 mg of granisetron, about 0.001 to about 2 g of finer glucose, and about 0.001 to about 2 g of coarser glucose. For example, the dry powder formulations may comprise about 0.5 to about 5 mg of granisetron, about 1 to about 200 mg of finer glucose, and about 1 to about 200 mg of coarser glucose.

In yet another particular embodiment, the dry powder formulations comprise granisetron, lactose, and glucose. The dry powder formulations comprising granisetron, lactose, and glucose may comprise granisetron, finer lactose, and coarser glucose or granisetron, finer glucose, and coarser lactose. For example, the dry powder formulations may comprise about 0.5 to about 5 mg of granisetron, from about 0.001 to about 2 g of lactose, and from about 0.001 to about 2 g of glucose. In one particular embodiment, the dry powder formulations comprise from about 0.5 to about 5 mg granisetron, from about 0.001 to 2 g of finer lactose, and from about 0.001 to about 2 g of coarser glucose. In an alternative embodiment, the formulation comprises from about 0.5 to about 5 mg of granisetron, from about 0.001 to about 2 g of finer glucose, and from about 0.001 to about 2 g of coarser lactose.

The aerosol formulations of the present invention are uniform and homogeneous. The uniformity/homogeneity of the aerosol formulations is measured by drawing 3 or more samples from the formulation, dissolving in mobile, and testing for concentration of the active pharmaceutical ingredient (API, granisetron) in the formulation by HPLC. The uniformity of the aerosol formulations is expressed by the relative standard deviation (% RSD) of the API concentration. The aerosol formulations have an RSD % less than 5%, less than 4%, less than 3%, less than 2.5%, less than 2.25%, less than 2.0%, less than 1.75%, less than 1.5%, less than 1.25%, less than 1.0%, less than 0.75%, less than 0.5%, less than 0.25%, and even less than 0.25%.

The discharge capacity or percent recovery of the aerosol formulations is measurable with a Next Generation Pharmaceutical Impactor (NGI). In this device, powders are drawn by vacuum into different chambers representing the lung, each chamber corresponding to a different range of aerodynamic particle size. NGI data includes mass median aerodynamic diameter (MMAD), and fine particle fraction (FPF). The FPF is generally assumed to represent the fraction of particles that would deposit in vivo in the "deep lungs," or particles that have an aerodynamic diameter of equal to or less than 5 µm. The discharge capacity or percent recovery of the aerosol formulations of the present invention is at least 70%, at least 75%, at least 80%, at least 85%, at least 90%, at least 91%, at least 92%, at least 93%, at least 94%, at least 95%, at least 96%, at least 97%, at least 98%, and even at least 99%, as measured by NGI.

The present inventors have observed that the inclusion of fine excipient particles increases the FPF while decreasing the MMAD. The inclusion of coarse excipient powders alone resulted in a FPF percent delivery of 7 to 8% where the coarse particles were lactose particles having a D10 of 3~6 µm, a D50 of 20~25 µm, and a D90 of 50~60 µm (LACTOHALE® 201 (LH201)), or lactose particles having a D10 of ~4 µm, a D50 of ~55 µm, and D90 a of ~170 µm (RESPITOSE® ML001 (ML001)). However, a combination of the coarse lactose particles ML001 (D10 of ~4 µm, a D50 of ~55 µm, and D90 a of ~170 µm) with fine lactose excipient particles having a D50<5 µm and a D90≤10 µm increased the FPF percent delivery. The FPF percent delivery increased further where the coarse particles that were mixed with the fine particle had a D10 of ~30 µm, a D50 of ~60 µm, and a D90 was ~100 µm (RESPITOSE® SV003 (SV003)).

In the present invention, each of the aerosol formulations containing coarse and fine lactose particles achieved a 3-5% increase in the delivery of FPF when the humidity of the environment during the aerodynamic performance testing was controlled to have a relative humidity (RH) of 50% rather than the ambient 20% RH. It is believed that the higher-than-ambient humidity, which is more representative of the environment in the human inhalation route, further increases the disaggregation by reducing the surface-energy-induced-aggregation when the formulation is inhaled into the impator.

Typically, the dry powdered formulations are administered by a dry powder inhaler, a dry powder dispenser, or a dry powder delivery device. The inhaler may be a single dose or multi-dose inhaler. Suitable inhalers may include SPINHALER®, ROTAHALER®, AEROLIZER®, INHALATOR®, HANDIHALER®, DISKHALER®, DISKUS®, ACCUHALER®, AEROHALER®, ECLIPSE®, TURBOHALER®, TURBUHALER®, EASYHALER®, NOVOLIZER®, CLICKHALER®, PULVINAL®, NOVOLIZER®, SKYEHALER®, XCELOVAIR®, PULVINA®, TAIFUN®, MAGHALER®, TWISTHALER®, JETHALER®, FLOWCAPS®, XCAPS®, TWINCAPS®, CYCLOHALER®, TURBOSPIN®, AIR DPI®, ORBITAL®, DIRECTHALER®, or an inhaler that is newly developed.

Pressurized Metered Dose Formulations (pMDI Formulations)

In another particular embodiment, the formulation is a pMDI formulation containing an excipient, where the excipient selected from the group consisting of oleates, stearates, myristates, alkylethers, alkyl arylethers, sorbates, and mixtures thereof. In the pMDI formulations, the excipient may include sorbitan trioleate, isopropyl myristate, or lecithin. Additional excipients for the pMDI formulations include oleic acid or oleic acid esters and polyvinylpyrrolidone (PVP).

In certain embodiments, the pMDI formulations do not include a propellant. However, the pMDI formulations generally include a propellant, especially a hydrofluoroalkane propellant. The hydrofluoroalkane propellants for the pMDI formulations are selected from the group consisting of 1,1,1,2-tetrafluoroethane (P134a), 1,1,1,2,3,3,3-heptafluoron propane (P227), and mixtures P134a and P227. Another suitable propellant for the pMDI formulations is 2H, 3H-perfluoropentane (HPFP).

The pMDI formulations may further include a diluent or a mixture of diluents. The pMDI formulations may also include a surfactant or a mixture of surfactants. Exemplary surfactants are selected from the group consisting of alkylethers, alkyl arylethers, laurates, myristates, oleates, sorbates, stearates, propylene glycol, lipids, and combinations thereof. Preferred surfactants are oleates, sorbates, stearates, propylene glycol, and combinations thereof.

In certain embodiments, the pMDI formulations do not comprise a co-solvent. However, in alternate embodiments, the pMDI formulations contain a co-solvent or a mixture of co-solvents. The pMDI formulations may include a co-solvent selected from $C_{2-6}$ alcohols, polyols, cineole, citral, lactic acid oligomers, or poly(ethylene glycols).

The pMDI formulations may comprises ethanol as a co-solvent. The content of ethanol in the pMDI formulations is no more than 25% (w/w), no more than 20% (w/w), no more than 15% (w/w), no more than 10% (w/w), no more than 8% (w/w), preferably no more than 5% (w/w) of ethanol, no more than 2.5% (w/w), and more preferably no more than 1% (w/w) of ethanol.

The content of the granisetron in the pMDI formulations is from about 0.01% to about 20%, from about 0.01% to about 10%, from 0.01% to about 5%, from about 0.01% to about 2%, from about 0.01% to about 1%, or from about 0.01% to about 0.5% of the total composition of the formulation. In a particular embodiment, with respect to the pMDI formulations, the content of the granisetron is from about 0.1% to about 0.2% of the total composition of the formulation.

In a particular embodiment, the pMDI formulations comprise granisetron and at least one selected from P134a and P227. In such pMDI formulations, based on the size of the canister, the amount of granisetron is from 0.1-100 mg, and the amount of P134a and/or P227 is about 0.5 g to about 50 g. In certain embodiments, the pMDI formulation contains granisetron and P134a, where the amount of granisetron is from about 0.1 to about 100 mg, preferably about 1-50 mg, and the amount of P134a is from 0.5 g to about 50 g, preferably about 10 g to 20 g. Similarly, the pMDI formulation may contains granisetron and P227, where the amount of granisetron is from about 0.1 to about 100 mg, preferably about 1-50 mg, and the amount of P227 is from 0.5 g to about 50 g, preferably about 10 g to 20 g. In pMDI formulations containing granisetron, P134a, and P227, the amount of granisetron is from about 0.1 to about 100 mg, preferably about 1-50 mg, the amount of P134a about 0.5 g to about 50 g, and the amount of P227 is about 0.5 g to about 50 g.

In further embodiments, the pMDI formulation comprises granisetron, P134a and/or P227, and isopropyl myristate. In certain embodiments, the pMDI formulations contain granisetron, P134a and/or P227, and propylene glycol. In addition, the pMDI formulations may contain granisetron, P134a and/or P227, and isopropyl laurate.

In certain embodiments, the pMDI formulations of the present invention contains granisetron that is a solute in a solution, and the solvent is selected from a group consisting of propellants, hybrid propellants, cosolvents, cosolvent mixture, organic solvents, water, buffers, and combinations thereof.

In certain embodiments, the pMDI formulations of the present invention contains granisetron that is in a powdered form in a suspension, and the suspension is in a liquid selected from a group consisting of propellants, hybrid propellants, propellants with stabilizers, propellants with surfactants, propellants with diluents, propellants with cosolvents, water, buffer, and combinations thereof.

In a particular embodiment, the pMDI formulations of the present invention contains granisetron that is a solute in a solution, wherein the solubility of granisetron is more than 0.01% w/w, more than 0.1% w/w, or more than 1%.

In a particular embodiment, the pMDI formulations of the present invention contains granisetron that is in a powdered form in a suspension, wherein the solubility of granisetron is less than 0.1% w/w, less than 0.01% w/w, less than 0.001%, or less than 0.0002% w/w.

Typically, the pMDI formulations are administered by an actuator, a metered dose inhaler, an aerosol dispenser, or an aerosol delivery device.

The present invention also provides methods of treating a condition of nausea or vomiting, wherein the method comprises pulmonary administration of a pharmaceutically acceptable amount of the aerosol formulations of the present invention; and wherein the formulations are administered into the pulmonary tract by inhalation. The pulmonary delivery of granisetron to a subject is carried out by having the subject inhale a pharmaceutically acceptable amount of the aerosol formulation of the present invention through the subject's mouth. Additionally or alternatively, the pulmonary delivery of granisetron to a subject is accomplished by having the subject inhale a pharmaceutically acceptable amount of the aerosol formulation of the present invention through the subject's nose.

In one embodiment, the pharmaceutically acceptable amount is produced by introducing the granisetron into a gas stream. Specifically, the pharmaceutically acceptable amount is produced by introducing the granisetron into a gas stream, and the gas stream is the subject's inspiratory breath.

In one embodiment, with respect to the methods, the pharmaceutically acceptable amount contains about 0.1 mg to about 25 mg of granisetron and the total dosage is from about 0.1 mg to about 25 mg.

Preferably, the pharmaceutically acceptable amount contains less than about 25 mg, less than about 20 mg, less than about 15 mg, less than about 10 mg, less than about 5 mg, or less than about 3 mg of granisetron. In another embodiment, the pharmaceutically acceptable amount contains more than about 0.1 mg, more than about 0.5 mg, more than about 1 mg, more than about 2 mg, or more than about 3 mg of granisetron. More preferably, the pharmaceutically acceptable amount contains about 3 mg of granisetron.

The total dosage of granisetron per day is about 0.1 mg to about 25 mg, about 0.2 mg to about 10 mg, about 0.5 mg to about 8 mg, about 1 mg to about 5 mg, about 2 mg to about 3 mg of granisetron per day.

With the dry powder formulations, the pharmaceutically acceptable amount of granisetron is produced by releasing blended powders containing powdered granisetron from a container such as a capsule or a blister by using a device such as a dry powder inhaler. A device may be loaded with one or more capsules/blisters at a time. The pharmaceutically acceptable amount is produced through one, two or multiple actuations. The releasing amount of one actuation is preferably equal to the formulation stored in one capsule or blister. Whereas with the pMDI formulations, the pharmaceutically acceptable amount of granisetron is produced by releasing a propellant containing granisetron from a container such as a canister by using a device such as a pMDI inhaler. The canister may be actuated by pressing an actuator or by inhalation. The pharmaceutically acceptable amount is produced through one, two or multiple actuations. The releasing amount of one actuation is preferably less than the formulation stored in one canister. The releasing amount is metered.

After administration to a subject, granisetron in blood plasma reaches a maximum concentration (Cmax) of 1-5000 ng/mL in the subject, preferably of 2-2000 ng/mL, and more preferably of 5-1000 ng/mL in a subject.

Delivery of the aerosol formulations through the pulmonary tract of a subject provides a Cmax of granisetron in blood plasma that is about 0.05 to about 1, about 0.1 to about 0.8, about 0.2 to about 0.6, or about 0.3 to about 0.4 times of the Cmax achieved following intravenous bolus delivery of granisetron. Moreover, delivery of the aerosol formulations through the pulmonary tract of a subject to provides a Cmax of granisetron in blood plasma that is about 0.1 to about 1.5, about 0.2 to about 1.25, about 0.4 to about 1.1, or about 0.8 to about 1.05 times of the Cmax achieved following oral delivery of granisetron.

In addition, the granisetron in blood plasma reaches maximum concentration at (Tmax) 1 minute to 2 hours after dose in a subject, preferably the Tmax is 2 minutes to 1 hour after dose in a subject, and even 5 minutes to 30 minutes after dose in a subject. Delivery of the aerosol formulations through the pulmonary tract of a subject provides a Tmax of granisetron in blood plasma that is about 0.01 to about 1.5, about 0.05 to about 1, about 0.1 to about 0.8, about 0.2 to about 0.6, or about 0.3 to about 0.4 times of the Tmax achieved following oral delivery of granisetron.

The area under curve (AUC) of granisetron in blood plasma of a subject ranges from 2-50000 ng*h/mL, preferably from 5-20000 ng*h/mL, and more preferably from 10-10000 ng*h/mL. Delivery of the aerosol formulations through the pulmonary tract produces a mean AUC of granisetron in blood plasma that is about 0.1 to about 1.5, about 0.2 to about 1.25, about 0.4 to about 1.1, or about 0.8 to about 1.05 times of the mean AUC achieved following intravenous bolus delivery of granisetron. In one embodiment, the AUC is about the same as that is achieved following intravenous bolus delivery of granisetron. Similarly, delivery of the aerosol formulations through the pulmonary tract produces a mean total AUC of granisetron in blood plasma that is about 0.1 to about 1.5, about 0.2 to about 1.25, about 0.4 to about 1.1, or about 0.8 to about 1.05 times of the AUC achieved following oral delivery of granisetron. In one embodiment, the AUC is about the same as that is achieved following oral delivery of granisetron.

In one embodiment, the aerosol and dry powder formulations and the method are useful for the reduction, elimination, or prevention of nausea and vomiting, where the nausea and vomiting are chemotherapy-induced nausea and vomiting, radiation-induced nausea, or vomiting and postoperative nausea and vomiting.

In one embodiment, the subject is a cancer patient; in particular, a cancer patient undergoing chemotherapy, radiotherapy, or a surgery. Additionally, the cancer patient may suffer from nausea and/or vomiting related to the chemotherapy, radiotherapy, or surgery.

The powdered granisetron of the aerosol formulations may be prepared by dissolving the bulk granisetron in distilled water with co-solvents, to form a solution; spray drying the solution, to obtain powered granisetron; separating and filtering the powdered granisetron according to their sizes with a cyclone; milling and grinding the powdered granisetron to further reduce the size of powered granisetron; and collecting and analyzing the precipitated granisetron powder. During the milling and grinding, the milling and grinding forces and timing are optimized so that the particle size distribution of the processed granisetron is from about 0.5 to about 5 μm; and the mean volume diameter is of about 2-3 μm.

The powdered granisetron of the aerosol and dry powder formulations may also be prepared by dissolving the bulk granisetron in distilled water, to form a solution; spray drying the solution with temperature in a drying vessel; separating and filtering the powdered granisetron according to their sizes with a cyclone; and collecting and analyzing the precipitated granisetron powder. The flow rate of the solution, the temperature and the flow rate of the drying air, and other parameters are optimized so that the granisetron precipitation is crystalline; and the particle size distribution is of about 0.5 to about 5 μm; and the mean volume diameter is of about 2-3 μm.

Alternatively, the powdered granisetron of the aerosol and dry powder formulations may be prepared by dissolving the bulk granisetron in supercritical fluid $CO_2$, to form a solution; depressuring the solution in a depressurization vessel; and collecting and analyzing the precipitated granisetron powder. The temperature and the pressure of the SCF $CO_2$ (before the precipitation) and the depressurization vessel, and other parameters are optimized so that the granisetron precipitation is crystalline; and the particle size distribution is of about 0.5 to about 5 μm; and the mean volume diameter is of about 2-3 μm.

For dry powder formulations, the powdered granisetron may be mixed with one or more excipients, to form the dry powder formulation. The obtained dry powder formulation is then loaded into a dry powder inhaler. Alternatively, for pMDI formulations, the granisetron may be mixed with a pressurized propellant or mixture of propellants, to form the pMDI formulation. The obtained pMDI formulation is then filled into canisters, which are installed into a metered-dose inhaler.

Thus, the present invention also provides pharmaceutical aerosol inhalation formulations or inhalable pharmaceutical aerosol formulations for pulmonary administration to a subject, wherein
  the formulation is a dry power formulation and comprises powdered granisetron;
  the powdered granisetron is produced by a particle engineering process;
  the MMAD of powdered granisetron is between 1 and 3 microns;
  the formulation may comprise excipient(s);
  the formulation is administered into the pulmonary tract by inhalation; and
  the subject is a cancer patient suffering from nausea that is related to chemotherapy, radiotherapy, or surgery;
  or the formulation is a pMDI formulation comprises granisetron;
  the granisetron may be powered granisetron produced by a particle engineering process;
  the MMAD of powdered granisetron is between 1 and 3 microns;
  the formulation may comprise excipient(s) and at least a hydrofluoroalkane;
  the formulation is administered into the pulmonary tract by inhalation; and
  the subject is a cancer patient suffering from nausea that is related to chemotherapy, radiotherapy, or surgery.

The powdered granisetron may be produced by a spray drying process that comprises:
  i) dissolving the bulk granisetron in distilled water, to form a solution;
  ii) spray drying the solution in a spray dryer;
  iii) separating and filtering the granisetron particles according to their sizes with a cyclone; and
  iv) collecting and analyzing the precipitated granisetron powder.

In another embodiment, the powdered granisetron is produced by a supercritical fluid process that comprises:
  i) dissolving the bulk granisetron in supercritical fluid $CO_2$, to form a solution;
  ii) depressuring the saturated solution in a depressurization vessel; and
  iii) collecting and analyzing the precipitated granisetron powder.

In one embodiment, the formulation is a pharmaceutical dry powder inhalation formulation that contains lactose and/or glucose as an excipient, where the amount of granisetron is about 0.05 to 100 wt %, about 1 to 50 wt %, about 2 to 20 wt %, or about 5 to 15 wt % of the excipient. In another embodiment, the formulation is a pharmaceutical pMDI inhalation formulation that contains P134a and/or P227 as propellants, where the amount of granisetron is about 0.01 to 20 wt %, about 0.01 to 1 wt %, or about 0.01 to 0.5 wt % of the propellant.

Delivery of the pharmaceutical aerosol inhalation formulations into the pulmonary tract of a subject provides a Cmax of granisetron in blood plasma that is about 20-80% of the Cmax achieved following intravenous bolus delivery of granisetron. The Cmax from delivery into the pulmonary tract may be about the same as the Cmax achieved following oral delivery of granisetron.

Delivery of the pharmaceutical aerosol inhalation formulations into the pulmonary tract of a subject provides Tmax of granisetron in blood plasma that is less than the Tmax achieved following oral delivery of granisetron.

Delivery of the pharmaceutical aerosol inhalation formulations into the pulmonary tract of a subject provides also provides an AUC of granisetron in blood plasma that is about the same as the AUC achieved following intravenous bolus or oral delivery of granisetron.

Additional embodiments within the scope provided herein are set forth in non-limiting fashion elsewhere herein and in the examples. It should be understood that these examples are for illustrative purposes only and are not to be construed as limiting in any manner.

Pulmonary Aerosol Formulations of the Present Invention

As described herein, the aerosol formulations of the present invention comprise granisetron and the formulations are useful for pulmonary delivery via inhalation. The active drug granisetron when administered by inhalation must penetrate deep into the lungs in order to show physiological action. In order to achieve this, the granisetron inhaled should be in the powdered form. Preferably, the MMAD of granisetron drug does not exceed about 5 µm.

Powdered Granisetron

The powdered granisetron can be prepared by processes of micronization, such as mechanical grinding, attrition by jet milling, solution precipitation, spray drying, lyophilization, and supercritical fluid processes.

Spray dying followed by a cyclone separation/filtering process may produce respirable particles rapidly and efficiently.

Direct controlled crystallization using an antisolvent precipitation technique may produce respirable particles with expected shapes. The particle size may be controlled by using one or more growth-retarding stabilizing additives.

Supercritical fluid processes may be used to produce respirable particles of the desired size. The supercritical processes may be used to prepare powdered granisetron may include rapid expansion, solution enhanced diffusion, gas-anti solvent, supercritical antisolvent, precipitation from gas-saturated solution, precipitation with compressed anti-solvent, aerosol solvent extraction system, or combinations of the foregoing. Particularly, the typical process can be rapid expansion of supercritical solution (RESS).

The powdered granisetron prepared by the above processes may have an MMAD between 0.5 and 5 µm.

The amount of the powdered granisetron in the formulation may be about 0.01% to about 100% of the total composition of formulation. Particularly, the amount of the powdered granisetron may be 0.05% to about 20% of the total composition of formulation.

Dry Powder Formulations

Excipients

The aerosol formulations of the present invention may comprise pharmaceutically acceptable excipients. The typical excipients which may be used in the formulation include carbohydrates, amino acids, polypeptides, lipids, salts, polyalcohols, galactose, mannose, sorbose, lactose, glucose, trehalose, raffinose, maltodextrins, dextrans, mannitol, xylitol, alanine, glycine, tryptophan, tyrosine, leucine, phenylalanine, and mixtures or combinations thereof.

pMDI Formulations

Propellants

The pMDI formulations of the present invention may comprise pharmaceutically acceptable propellants. Typical propellants include hydrofluoroalkane (HFA) propellants. The hydrofluoroalkane propellants which may be used in the pMDI formulations include 1,1,1,2-tetrafluoroethane (P134a), 1,1,1,2,3,3,3-heptafluoro-n propane (P227), and mixtures of P134a and P227.

Surfactants

The pMDI formulations of the present invention may comprise pharmaceutically acceptable surfactants. Typical surfactants include alkylethers, alkyl arylethers, laurates, myristates, oleates, sorbates, stearates, propylene glycol, lipids, and combinations thereof.

Co-Solvents

The pMDI formulations of the present invention may comprise pharmaceutically acceptable co-solvents. Typical co-solvents include $C_{2-6}$ alcohols, polyols, and combinations thereof. Particularly, the co-solvent may be ethanol.

Exemplary Formulations of the Invention

The following examples illustrate certain embodiments of the disclosure and are not intended to be construed in a limiting manner.

Exemplary Formulations of the Invention

Formulation 1

| Ingredient | Amount |
| --- | --- |
| Granisetron Fine Powder | 5 mg |

Formulation 2

| Ingredient | Amount |
| --- | --- |
| Granisetron Fine Powder | 5 mg |
| Lactose Powder | 45 mg |

Formulation 3

| Ingredient | Amount |
| --- | --- |
| Granisetron Fine Powder | 5 mg |
| Glucose Powder | 45 mg |

Formulation 4

| Ingredient | Amount |
| --- | --- |
| Granisetron Fine Powder | 2 mg |
| Lactose Powder | 18 mg |

Formulation 5

| Ingredient | Amount |
| --- | --- |
| Granisetron Fine Powder | 5 mg |
| Finer Lactose Powder | 4.5 mg |
| Coarser Lactose Powder | 40.5 mg |

Formulation 6

| Ingredient | Amount |
| --- | --- |
| Granisetron Fine Powder | 2 mg |
| Glucose Powder | 18 mg |

Formulation 7

| Ingredient | Amount |
| --- | --- |
| Granisetron Fine Powder | 5 mg |
| Finer Glucose Powder | 4.5 mg |
| Coarser Glucose Powder | 40.5 mg |

Formulation 8

| Ingredient | Amount |
| --- | --- |
| Granisetron Fine Powder | 2 mg |
| Lactose Powder | 9 mg |
| Glucose Powder | 9 mg |

Formulation 9

| Ingredient | Amount |
| --- | --- |
| Granisetron | 20 mg |
| HFA 134a Propellant | 10 g |

Formulation 10

| Ingredient | Amount |
| --- | --- |
| Granisetron | 20 mg |
| HFA 134a Propellant | 10 g |
| Isopropyl Myristate | 0.1 g |

Formulation 11

| Ingredient | Amount |
| --- | --- |
| Granisetron | 20 mg |
| HFA 227 Propellant | 10 g |

Formulation 12

| Ingredient | Amount |
| --- | --- |
| Granisetron | 20 mg |
| HFA 227 Propellant | 10 g |
| Isopropyl Myristate | 0.1 g |

Formulation 13

| Ingredient | Amount |
| --- | --- |
| Granisetron | 20 mg |
| HFA 134a Propellant | 20 g |

Formulation 14

| Ingredient | Amount |
| --- | --- |
| Granisetron | 20 mg |
| HFA 227 Propellant | 20 g |

Formulation 15

| Ingredient | Amount |
| --- | --- |
| Granisetron | 20 mg |
| HFA 134a Propellant | 10 g |
| HFA 227 Propellant | 10 g |

Formulation 16

| Ingredient | Amount |
| --- | --- |
| Granisetron | 20 mg |
| HFA 134a Propellant | 10 g |
| HFA 227 Propellant | 10 g |
| Isopropyl Laurate | 0.1 g |

Formulation 17

| Ingredient | Amount |
| --- | --- |
| Granisetron | 2 mg |
| HFA 134a Propellant | 1 g |

Formulation 18

| Ingredient | Amount |
| --- | --- |
| Granisetron | 2 mg |
| HFA 134a Propellant | 1 g |
| Isopropyl Myristate | 0.01 g |

Formulation 19

| Ingredient | Amount |
| --- | --- |
| Granisetron | 2 mg |
| HFA 227 Propellant | 1 g |

Formulation 20

| Ingredient | Amount |
| --- | --- |
| Granisetron | 2 mg |
| HFA 227 Propellant | 1 g |
| Isopropyl Myristate | 0.01 g |

Formulation 21

| Ingredient | Amount |
| --- | --- |
| Granisetron | 2 mg |
| HFA 134a Propellant | 2 g |

Formulation 22

| Ingredient | Amount |
| --- | --- |
| Granisetron | 2 mg |
| HFA 227 Propellant | 2 g |

Formulation 23

| Ingredient | Amount |
| --- | --- |
| Granisetron | 2 mg |
| HFA 134a Propellant | 1 g |
| HFA 227 Propellant | 1 g |

Formulation 24

| Ingredient | Amount |
| --- | --- |
| Granisetron | 2 mg |
| HFA 134a Propellant | 1 g |
| HFA 227 Propellant | 1 g |
| Isopropyl Laurate | 0.01 g |

Example 1: Preparation of Spray Dried Granisetron Fine Powder

Powdered granisetron was prepared by spray drying with SPRAY DRYER SD-MICRO™ (manufactured by GEA Process Engineering, Inc., Columbia, Md., USA). The experiments were done at GEA Process Engineering, Inc., Columbia, Md., USA.

TABLE 1

Parameters of Spray Drying to Prepare Granisetron Fine Powder

| Run | Conc. (wt %) | $N_2$ (kg/hr) | Inlet Temp. (° C.) | Outlet Temp. (° C.) | Spray Rate (g/min) | Nozzle Diameter (mm) |
| --- | --- | --- | --- | --- | --- | --- |
| 1 | 2.94 | 30 | 170 | 85 | 10.6 | 0.5 |
| 2 | 2.94 | 30 | 170 | 85 | 10.9 | 0.5 |
| 3 | 2.94 | 30 | 195 | 100 | 9.9 | 0.5 |

Example 2: Particle Size Distribution of Spray Dried Granisetron Fine Powder

The Particle Size Distribution of the Granisetron Fine Powder, prepared by Spray Drying using the above parameters was measured by Malvern Mastersizer (Malvern Instruments, UK) at GEA Process Engineering, Inc., Columbia, Md., USA.

The typical Particle Size Distribution:
D10: 1.01 μm
D50: 2.33 μm
D90: 5.34 μm
Cumulative % on <9 μm: 98.0%

Figure 2:
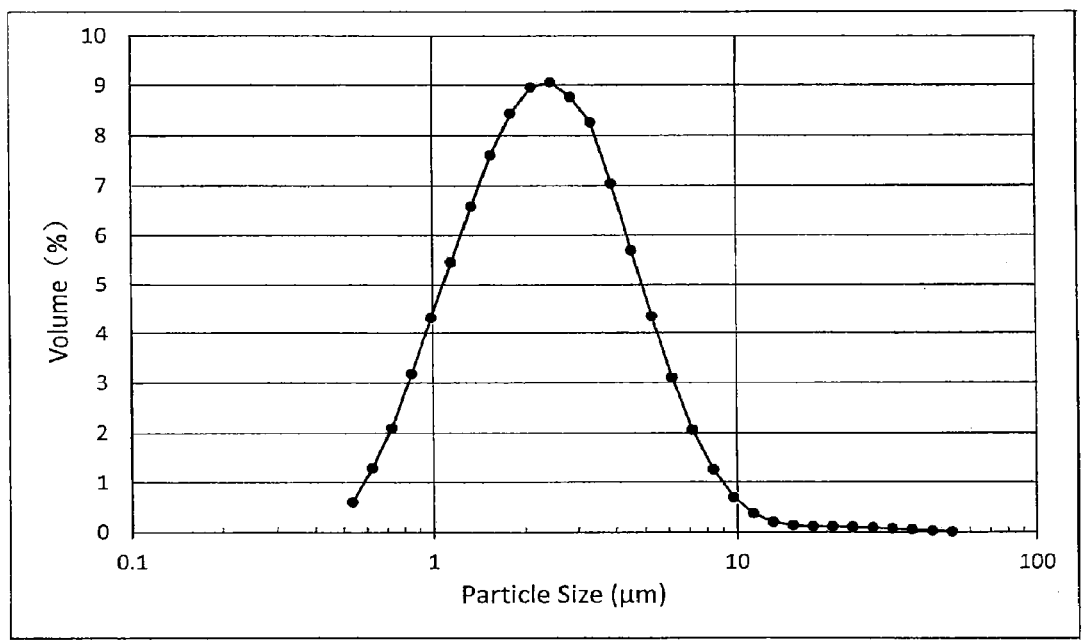
FIG. 2: A typical particle size distribution of spray dried granisetron powder.

FIG. 2 shows the typical Particle Size Distribution of the Spray Dried Granisetron.

Example 3: Preparation of Jet Milled Granisetron Fine Powder

Granisetron HCl was milled with a Model-00 JET-O-MIZER (manufactured by Fluid Energy Processing and Equipment Company). Pushing nozzle and grinding nozzle pressure were both set to 110 psi. The granisetron HCl particles were milled for 5 cycles and the particles were measured after the first, third, and fifth cycles. After 5 cycles, it was determined that the particle size would not continue to decrease with additional milling. The jet milling experiments were conducted at Drug Dynamics Institute, College of Pharmacy, The University of Texas at Austin, Austin, Tex., USA.

Example 4: Particle Size Distribution of Jet Milled Granisetron Fine Powder

The particle size distributions of the jet milled granisetron fine powder were measured after the first cycle, the third cycle, and the fifth cycle of jet milling with the above parameters. The particle size distributions were measured by Malvern Spraytec (Malvern Instruments, UK) operated at 90LPM during over a 4 second duration. The experiments were done at Drug Dynamics Institute, College of Pharmacy, The University of Texas at Austin, Austin, Tex., USA.

The typical particle size distribution of the milled granisetron is shown in Table 2.

TABLE 2

Particle size distribution of jet milled granisetron as a function of milling

| Milling Cycle | D10 | D50 | D90 |
|---|---|---|---|
| 0 | 3.77 μm | 50.21 μm | 445.02 μm |
| 1 | 2.22 μm | 7.01 μm | 20.59 μm |
| 3 | 1.44 μm | 3.99 μm | 9.90 μm |
| 5 | 1.59 μm | 3.79 μm | 8.13 μm |

Figure 3:
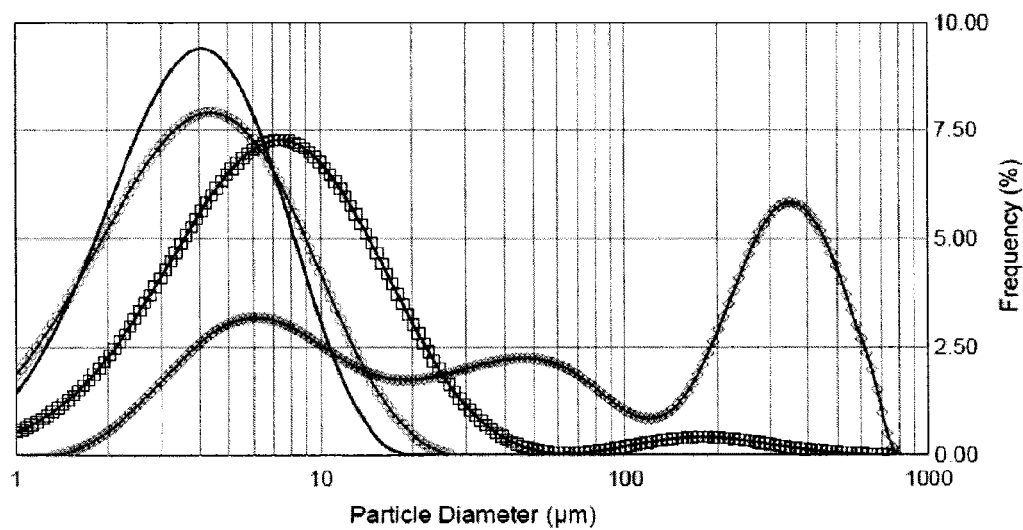
FIG. 3: A typical particle size distribution of jet milled granisetron powder.
Figure 4:
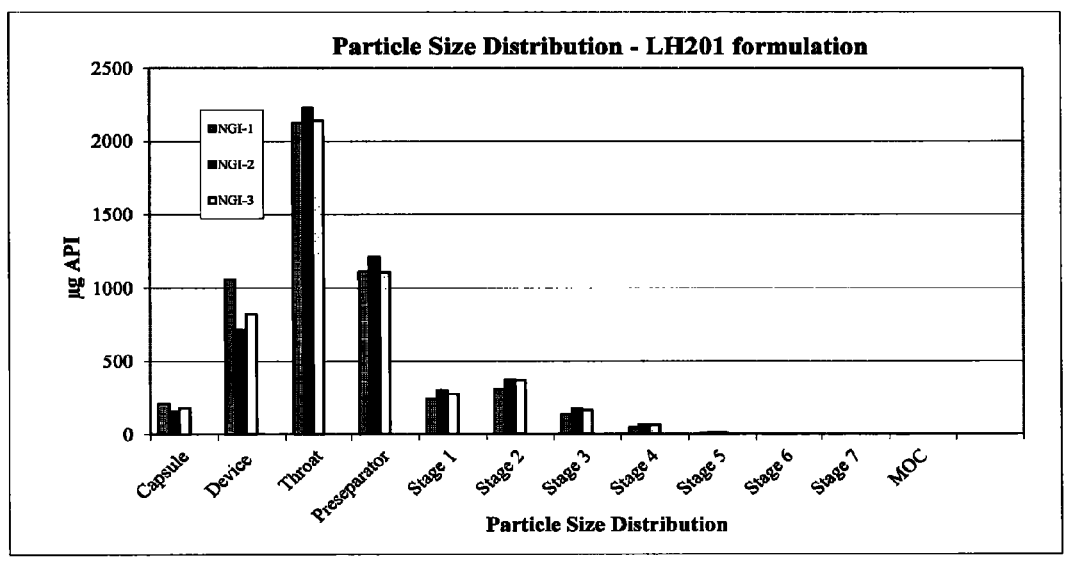
FIG. 4: The aerosol particle size distribution (ASPD) of 3 runs of the LH201 blend at 60 LPM and under ambient temperature and humidity conditions of ~22° C. and 20% RH.
Figure 5:
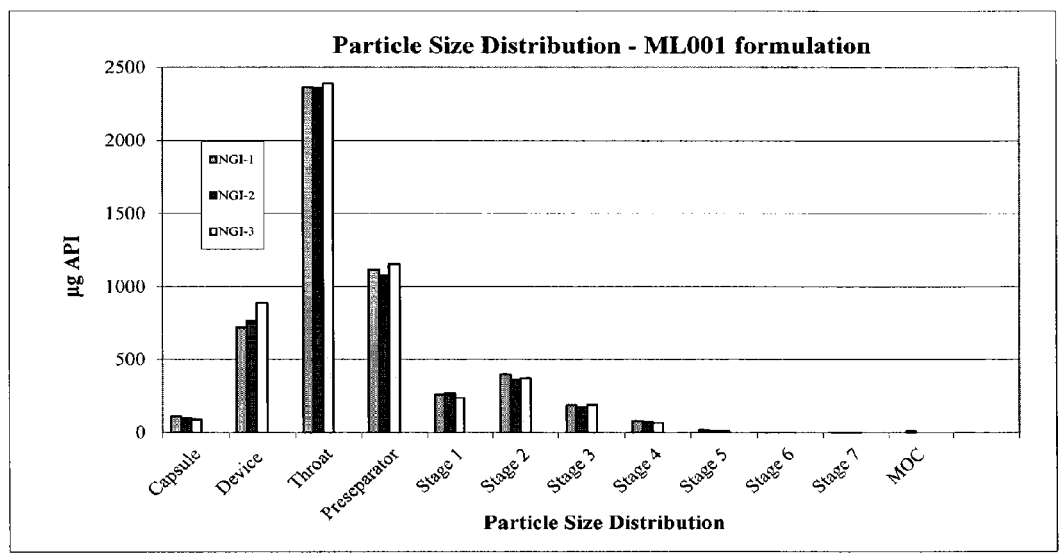
FIG. 5: The ASPD of 3 runs of the ML001 blend at 60 LPM and under ambient temperature and humidity conditions of ~22° C. and 20% RH.
Figure 6:
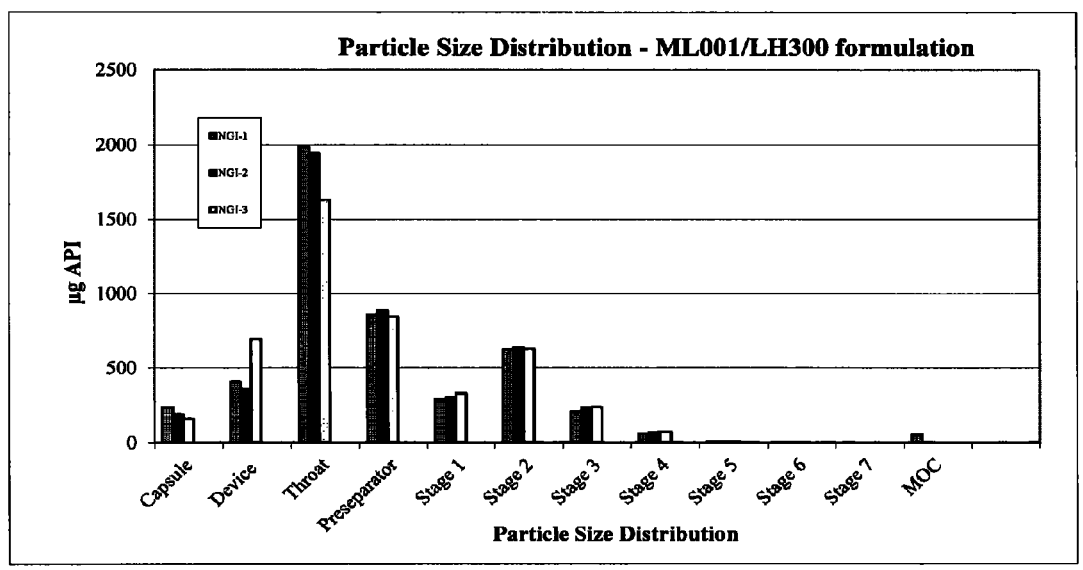
FIG. 6: The ASPD of 3 runs of the ML001/LH300 blend at 60 LPM and under ambient temperature and humidity conditions of ~22° C. and 20% RH.
Figure 7:
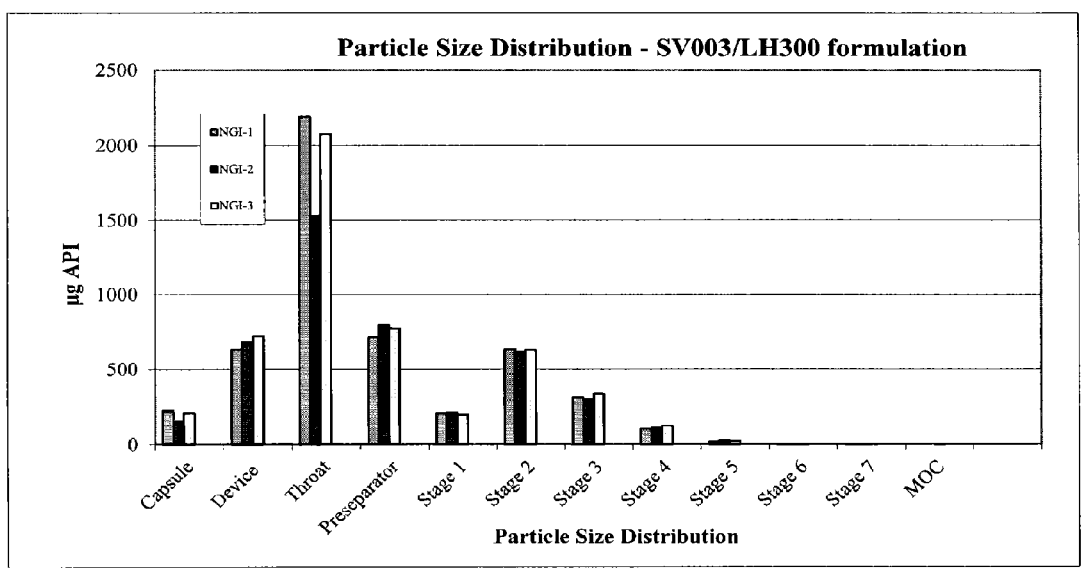
FIG. 7: The ASPD of 3 runs of the SV003/LH300 blend at 60 LPM and under ambient temperature and humidity conditions of ~22° C. and 20% RH.

FIG. 3 shows the typical particle size distribution of the jet milled granisetron as a function of milling cycle. As shown in FIG. 3, the d50 after the fifth milling cycle was 3.79 μm, which is within the respirable range. Furthermore, approximately 75% of the mass was less than 5 μm in diameter.

Example 5: Fine Particle Fraction by Next Generation Impaction

The fine particle fraction (FPF) of the dry powder granisetron aerosol formulations was measured by Next Generation Impaction (NGI) at Drug Dynamics Institute, College of Pharmacy, The University of Texas at Austin, Austin, Tex., USA.

The in vitro aerodynamic performance of the dry powder granisetron aerosol formulations were tested by NGI. The results reflect the in vivo (pulmonary) aerodynamic performance of the following aerosol formulations. The Next Generation Impactor used in this embodiment was made by Copley Scientific, GB.

The Exemplary Formulation 1 (EF1) measured by NGI included:
Milled Granisetron (MG): 5 mg;
Coarse Lactose (LH201): 45 mg;
Fine Lactose: N/A.

The Exemplary Formulation 2 (EF2) that was measured by NGI was:
Milled Granisetron (MG): 5 mg;
Coarse Lactose (ML001): 45 mg;
Fine Lactose: N/A.

The Exemplary Formulation 3 (EF3) that was measured by NGI was:
Milled Granisetron (MG): 5 mg;
Coarse Lactose (ML001): 40.5 mg;
Fine Lactose (LH300): 4.5 mg.

The Exemplary Formulation 4 (EF4) that was measured by NGI was:
Milled Granisetron (MG): 5 mg;
Coarse Lactose (SV300): 40.4 mg;
Fine Lactose (LH300): 4.5 mg.

The lactose in the EF1 was LACTOHALE® 201 (LH201; D10 was 3~6 μm, D50 was 20~25 μm, D90 was 50~60 μm) made by DFE Pharma, Germany. The lactose in EF2 was RESPITOSE® ML001 (ML001, milled; D10 was ~4 μm, D50 was ~55 μm, D90 was ~170 μm) made by DFE Pharma, Germany. The lactose in EF3 was a mixture of RESPITOSE® ML001 and LACTOHALE® 300 (LH300, micronized; D50 was <5 μm, D90 was ≤10 μm) made by DFE Pharma, Germany. The Lactose in EF4 was a mixture of RESPITOSE® SV003 (SV003, sieved; D10 was ~30 μm, D50 was ~60 μm, D90 was ~100 μm) made by DFE Pharma, Germany and LACTOHALE® 300.

Each of the EF blends were produced with a TURBULA® Shaker Mixer. For the blends that included fines (e.g., ML001/LH300), the coarse lactose and the fine lactose were blended together before the addition of the granisetron. All blending was performed at 48 rpm for 2 cycles of 15 minutes. After a blending cycle was complete, the contents were passed through a 300 μm aperture sieve. All blends produced were tested for Batch Uniformity/Potency. Batch Uniformity/Potency was tested by drawing 3 samples from each blend. Each sample was measured by HPLC in triplicate. A % RSD below 2.5% was considered adequate uniformity for this study. Potency was calculated as an average of all 9 measurements. % RSD was also based on all 9 measurement.

TABLE 3

Blend Uniformity and Potency Testing

| | LH201 | ML001 | ML001/LH300 | SV003/LH300 |
|---|---|---|---|---|
| Potency (%) | 10.55 | 10.25 | 9.63 | 10.03 |
| % RSD | 0.12 | 1.62 | 2.15 | 0.58 |

HandiHaler® was used as the model Dry Powder Inhaler Device. The flow rate was 60 LPM (>4 kPa), the duration was 4 seconds, the total volume was 4 L. Testing was performed under ambient and controlled environment conditions. All four exemplary aerosol formulations (EF1, EF2, EF3, and EF4) were tested at ambient conditions. The ambient conditions were approximately 22° C. and 20% relative humidity (RH). Both formulations containing fine lactose (EF3 and EF4) were also tested at the controlled environment conditions. The controlled environment conditions were 23° C. and 50% RH.

The number of NGI runs at ambient conditions were: EF1, n=3; EF2, n=3; EF3, n=3; and EF4, n=3.

All NGI runs under ambient conditions exhibited a percent recovery greater than 90%. Aerosol particle size distribution (APSD) of individual NGI runs are given in FIGS. 4-7. Mean aerosol performance data are given in Table 4.

TABLE 4

The Mean APSD Parameters of EF1-EF4 Measured by NGI at ~22° C. and 20% RH.

| Parameter (Unit) | EF1 | RSD (%, EF1) | EF2 | RSD (%, EF2) | EF3 | RSD (%, EF3) | EF4 | RSD (%, EF4) |
|---|---|---|---|---|---|---|---|---|
| Amount of Drug Loaded ($\mu$g) | 5340 | 1 | 5272 | 3 | 5116 | 2 | 5300 | 1 |
| % Recovered | 98 | 1 | 100 | 1 | 91 | 2 | 92 | 8 |
| Preseparator, % of Loaded | 21 | 5 | 21 | 1 | 17 | 2 | 14 | 5 |
| Delivered Dose, % of Loaded | 78 | 5 | 83 | 1 | 78 | 3 | 75 | 7 |
| Fine Particle Fraction ($\leq 5$ $\mu$m), % of Delivered | 7 | 8 | 8 | 4 | 11 | 4 | 15 | 8 |
| Mass Median Aerodynamic Diameter($\mu$m) | 6 | <1 | 6 | 2 | 6 | 1 | 5 | 2 |

The FPF of EF1-EF4 under ambient conditions were 7, 8, 11, and 15%, respectively. FPF was defined as percent of particles less than 5 $\mu$m. The MMAD of EF1-EF4 under ambient conditions was 6 $\mu$m, 6 $\mu$m, 6 $\mu$m, and 5 $\mu$m, respectively.

Notably, the inclusion of fines increased the FPF, and reduced the MMAD. EF4, the blend of RESPITOSE® SV003 and LACTOHALE® 300, exhibited the highest FPF and the lowest MMAD.

The numbers of NGI runs at the controlled environment conditions (23° C., 50% RH) were: EF3, n=3; and EF4, n=3.

Figure 8:
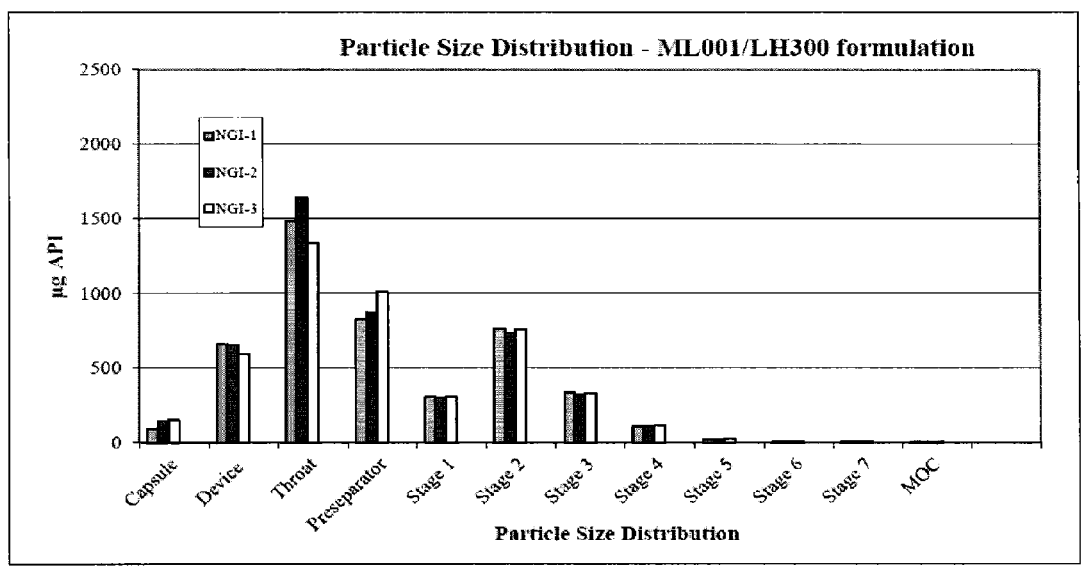
FIG. 8: The ASPD of 3 runs of the ML001/LH300 blend at 60 LPM and at a controlled temperature and humidity of 23° C. and 50% RH, respectively.
Figure 9:
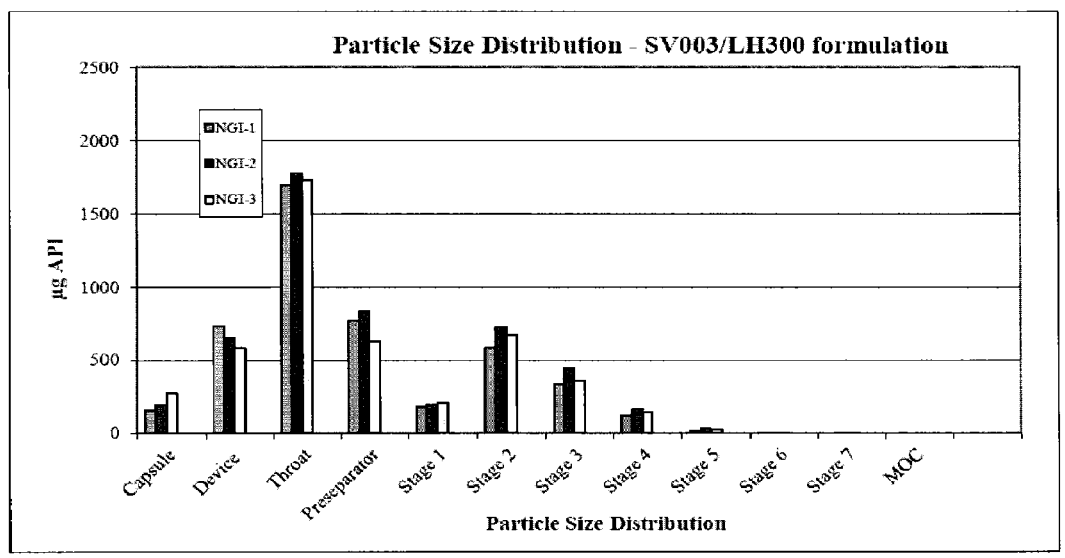
FIG. 9: The ASPD of 3 runs of the SV003/LH300 blend at 60 LPM and at a controlled temperature and humidity of 23° C. and 50% RH, respectively.

All NGI runs under the controlled environment conditions exhibited a percent recovery greater than 90%. Aerosol particle size distribution (APSD) of individual NGI runs are given in FIGS. 8 and 9. Mean aerosol performance data are given in Table 5.

TABLE 5

The Mean APSD Parameters of EF1-EF4 Measured by NGI at ~22° C. and 20% RH.

| Parameter (Unit) | EF3 | RSD (%, EF3) | EF4 | RSD (%, EF4) |
|---|---|---|---|---|
| Amount of Drug Loaded ($\mu$g) | 5006 | 1 | 5061 | 3 |
| % Recovered | 93 | 2 | 93 | 2 |
| Preseparator, % of Loaded | 18 | 10 | 15 | 13 |
| Delivered Dose, % of Loaded | 78 | 1 | 76 | 4 |
| Fine Particle Fraction ($\leq 5$ $\mu$m), % of Delivered | 16 | 5 | 18 | 9 |
| Mass Median Aerodynamic Diameter($\mu$m) | 5.6 | 0.4 | 5.0 | 2.1 |

The FPF of EF3 and EF4 under the controlled environment conditions 16 and 18%, respectively. FPF was defined as percent of particles less than 5 $\mu$m. The MMAD of EF3 and EF4 under the controlled environment conditions was 5.6 $\mu$m and 5.0 $\mu$m, respectively.

A comparison between the EF3 and EF4 at ambient conditions (~22° C., 20% RH) versus the controlled environment conditions (23° C., 50% RH) shows a further increase in the FPF, but also a decrease in the deposition levels in the throat of the NGI.

In comparing all of the aerosol formulations at ambient and controlled conditions, EF4, the blend of RESPITOSE® SV003 and LACTOHALE® 300, exhibited the highest FPF and the lowest MMAD. Both aerosol formulations containing fine lactose, EF3 (ML001/LH300) and EF4 (SV003/LH300) demonstrated a further improvement in performance when tested at 50% RH rather than 20% RH. The average FPF of EF4 (SV003/LH300) at 20% RH and 50% RH was 15% and 18%, respectively.

Example 6: Solubility of Granisetron in pMDI Formulations

The solubility of granisetron was measured in a pMDI medium of HFA 134 as well as a mixture of HFA 134 and ethanol.

The solubility results with HFA 134 alone were as follows:

| pMDI Medium | ~24 Hours | 10 days |
|---|---|---|
| HFA 134a ($\mu$g/mL) | 2.370 | 13.16 |
| | 3.808 | 14.84 |
| | 0.336 | 10.26 |
| | — | 11.51 |
| | — | 15.77 |
| Average (RSD) | 2.171 (0.803) | 13.11 (0.174) |

As shown above, the solubility of the granisetron in a propellant alone, HFA 134a, was 2.171 $\mu$g/mL after 24 hours, and 13.11 $\mu$g/mL after 10 days. Since the gravity of the HFA 134a is 1.21 g/mL, the above results are equal to 0.00018% w/w and 0.00108% w/w, respectively after 24 hours and 10 days.

The solubility of granisetron in a mixture of HFA 134 and a cosolvent, ethanol, was also conducted. As shown in the following Table, the solubility results were 85.483 $\mu$g/mL after 24 hours, and 82.36 $\mu$g/mL after 10 days. The results are equal to 0.00706% w/w, and 0.00681% w/w respectively.

| pMDI Medium | ~24 Hours | 10 days |
|---|---|---|
| HFA 134a with Ethanol (9:1) ($\mu$g/mL) | 90.781 | 79.88 |
| | 84.173 | 74.29 |
| | 81.496 | 86.6 |
| | — | 97.99 |
| | — | 73.93 |
| Average (RSD) | 85.483 (0.056) | 82.36 (0.125) |

From the foregoing description, various modifications and changes in the compositions and methods provided herein will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

REFERENCES

Hornby, P (2001). "Central neurocircuitry associated with emesis". The American Journal of Medicine 111 (8): 106S-112S. PMID 11749934

Aapro, M. (2004). "Granisetron: an update on its clinical use in the management of nausea and vomiting". Oncologist 9 (6): 673-686. PMID 15561811

Chow, A. H.; Tong, H. H.; Chattopadhyay, P.; Shekunov, B. Y. (2007). "Particle engineering for pulmonary drug delivery". Pharmaceutical Research 24 (3): 411-437. PMID 17245651

The invention claimed is:

1. A dry powder aerosol formulation for use in a dry powder inhaler, comprising:
   granisetron having a mean geometric diameter of 1-3 microns; and
   a pharmaceutically acceptable excipient,
   wherein the excipient is a mixture of coarse and fine particle lactose; and wherein the coarse particle lactose has a D50 of about 55 μm or about 60 μm; and wherein the fine particle lactose has a D50 of less than 5 μm.

2. A method of treating nausea or vomiting, the method comprising:
   administering the formulation of claim 1 to a subject in need thereof, wherein the formulation is administered into the pulmonary tract of the subject by inhalation.

3. The formulation of claim 1, wherein the coarse lactose particle has a D10 of about 4 μm and D90 of about 170 μm.

4. The formulation of claim 1, wherein the fine particle lactose has a D90 of equal to or less than 10 μm.

5. The formulation of claim 1, wherein ondansetron is about 15% of total composition of the formulation, or about 10% of the total composition of the formulation, or about 5% of the total composition of the formulation.

6. The formulation of claim 1 wherein the ratio of granisetron to lactose is about 1:9.

7. The formulation of claim 1, wherein the ratio of coarse to fine lactose is about 9:1.

8. The formulation of claim 1, wherein granisetron is more than about 0.1 mg and less than about 10 mg.

9. The formulation of claim 1, wherein granisetron is more than about 0.5 mg and less than about 5 mg.

10. The formulation of claim 1, wherein the mass median aerodynamic diameter (MMAD) of ondansetron is between 0.5 and 5 microns.

11. The formulation of claim 1, wherein the mass median aerodynamic diameter (MMAD) of ondansetron is at least 2 microns; and at most 3.5 microns.

12. The formulation of claim 1, wherein the formulation has a fine particle fraction (FPF) of at least 10% to at most 30%, when tested using a Next Generation Impactor (NGI).

13. The formulation of claim 1, wherein the formulation has a respirable fraction (RPF) of 20% or more, when tested using a Next Generation Impactor (NGI).

* * * * *